(12) United States Patent
Prasad et al.

(10) Patent No.: US 7,884,937 B2
(45) Date of Patent: Feb. 8, 2011

(54) AIRBORNE TUNABLE MID-IR LASER GAS-CORRELATION SENSOR

(75) Inventors: Coorg Rangaswamy Prasad, Silver Spring, MD (US); Bo Lin, Fairfax, VA (US); Hyo Sang Lee, Silver Spring, MD (US)

(73) Assignee: Science & Engineering Services, Inc., Columbia, MD (US)

( * ) Notice: Subject to any disclaimer, the term of this patent is extended or adjusted under 35 U.S.C. 154(b) by 742 days.

(21) Appl. No.: 11/737,547

(22) Filed: Apr. 19, 2007

(65) Prior Publication Data

US 2008/0259340 A1   Oct. 23, 2008

(51) Int. Cl.
G01N 21/00 (2006.01)
G01J 5/00 (2006.01)
G01J 5/02 (2006.01)

(52) U.S. Cl. ............... 356/437; 250/338.1; 250/338.5; 250/339.11; 250/339.12; 250/339.13; 250/341.8

(58) Field of Classification Search ............ None
See application file for complete search history.

(56) References Cited

U.S. PATENT DOCUMENTS

| | | | | |
|---|---|---|---|---|
| 3,853,407 | A * | 12/1974 | Dewey, Jr. | 356/320 |
| 4,061,918 | A * | 12/1977 | Preier et al. | 250/343 |
| 4,853,543 | A * | 8/1989 | Ozdemir | 250/372 |
| 5,930,000 | A * | 7/1999 | Brand | 356/437 |
| 6,683,894 | B1 | 1/2004 | Lee et al. | |
| 6,750,453 | B1 * | 6/2004 | Nelson et al. | 250/338.5 |

(Continued)

FOREIGN PATENT DOCUMENTS

WO    WO 8601295 A   *   2/1986

OTHER PUBLICATIONS

H.S. Lee, et al. "Gas Filter Correlation Instrument for the Remote Sensing of Gas Leaks", Review of Scientific Instruments, vol. 56, No. 9, pp. 1812-1819, Sep. 1985.

(Continued)

*Primary Examiner*—Tarifur Chowdhury
*Assistant Examiner*—Gordon J Stock, Jr.
(74) *Attorney, Agent, or Firm*—Oblon, Spivak, McClelland, Maier & Neustadt, L.L.P.

(57) ABSTRACT

A method and apparatus for measuring target gas concentrations in an atmosphere. The method and apparatus emit in the atmosphere a laser beam tuned to a molecular absorption line of a target gas, receive a reflected signal affected by gas absorption of the target gas in the atmosphere, divide and direct the received signal into a first optical path and a second optical path including in one of the paths a correlation gas cell filled with a predetermined concentration of the target gas, detect transmitted signals through the first optical path and the second optical path, and calculate a target gas concentration by comparing a first signal transmitted through the first optical path to a second signal transmitted through the second optical path. The apparatus includes a laser source tunable to a specific molecular absorption line of a target gas and configured to emit in the atmosphere a laser beam having a spectral bandwidth greater than a full width of the molecular absorption line of the target gas, a receiver configured to receive a reflected signal affected by gas absorption of the target gas in the atmosphere, and at least one detector configured to detect transmitted signals through the first optical path and the second optical path.

18 Claims, 11 Drawing Sheets

U.S. PATENT DOCUMENTS

| | | | |
|---|---|---|---|
| 6,822,236 B1 * | 11/2004 | Nelson et al. | 250/338.5 |
| 6,853,452 B1 * | 2/2005 | Laufer | 356/436 |
| 7,655,910 B2 * | 2/2010 | Kajii | 250/343 |
| 2002/0071122 A1 * | 6/2002 | Kulp et al. | 356/437 |
| 2008/0144677 A1 * | 6/2008 | Belkin et al. | 372/20 |

OTHER PUBLICATIONS

T. V. Ward, et al., "Gas Cell Correlation Spectrometer: Gaspec", Applied Optics, vol. 14, No. 12, pp. 2896-2904, Dec. 1975.

Avishai Ben-David, "Optimal Bandwidth for Topographical Differential Absorption Lidar Detection", Applied Optics, vol. 35, No. 9, pp. 1531-1536, Mar. 20, 1996.

Russell E. Warren, "Optimum Detection of Multiple Vapor Materials With Frequency-Agile Lidar", Applied Optics, vol. 35, No. 21, pp. 4180-4193, Jul. 20, 1996.

Narasimha S. Prasad, et al., "Remote Sensing of Propane and Methane by Means of Differential Absorpotion Lidar by Topographic Reflection", Optical Engineering, vol. 35, No. 4. Apr. 1996. pp. 1105-1111.

Coorg R. Prasad et al., "Tunable IR Differential Absorpition Lidar for Remote Sensing of Chemicals", Application of Lidar to Current Atmospheric Topics <xml:namespaceprefix = st 1 ns = "urn:schemas-microsoft-com:office:smarttags" />III, SPIE, vol. 3757, pp. 87-95, Jul. 1999.

John R. Quagliano, et al., "Quantitative Chemical Identification of Four Gases in Remote Infrared (9-11 μm) Differential Absorpiton Lidar Experiments", Applied Optics, vol. 36, No. 9, pp. 1915-1927, Mar. 20, 1997.

Jonas Sandsten, et al., "Gas Imaging by Infrared Gas-Correlation Spectrometry", Optics Letters, vol. 21, No. 23, pp. 1945-1947, Dec. 1, 1996.

* cited by examiner

Table 1

| Q-switched Yb:YAG Laser for Pumping OPO ||
|---|---|
| Pump Laser Diode | InGaAs, 940 nm arrays |
| Pump Diode Power | 450 W array stacks |
| Yb:YAG Laser crystal | 15 % Yb, 1.5 × 3 × 6 mm |
| Output Energy | 7 to 8 mJ |
| Repetition Rate | 100 Hz |
| Pulse Duration | 25 to 40 ns |
| Output Wavelength | 1027 to 1033 nm |
| Output Line width | 0.5 nm |
| Pump Tuned Mid-IR PPRTA OPO ||
| Output Energy | 1 mJ |
| Idler wavelength Range | 2.8 to 4.2 µm |
| OPO Line width | 3 to 6 nm |

Figure 7

Table 2

| $E_L$ | Laser energy | 0.5 mJ/pulse |
|---|---|---|
| A | Detector area | 0.31 m² |
| R | Range | 1 km |
| η | Optical efficiency | 0.5 |
| Φ(R) | Overlap function | 1.0 at 1 km |
| ρ | Surface reflectance | 0.1 |
| D* | Detectivity | $4.1 \times 10^{10}$ cm/Hz$^{½}$ W |
| NEP | Noise equivalent power | 9.7 nW |
| $E_s$ | Signal received | Tr × $1.27 \times 10^{-13}$ J |

Figure 8

Table 3

| Mid-IR laser | 1 mJ at 3μm, 100 Hz, 2.7 to 4 μm, 1 mrad divergence | |
|---|---|---|
| Receiver | 200 mm diameter telescope with gold coated mirrors | |
| Detector | 3 to 3.8 μm: InAs, TEC Cooling | |
| Optical Filter | 3.427 μm Bandpass: ± 5 nm | |
| Gas correlation Cell | 25 mm diameter, 20 mm long 1 atmosphere of methane | |
| Range to the Earth's surface | 1 km | 200 m |
| Measurement Sensitivity | Methane 14 ppm·m @ 1 km | Methane 0.5 ppm·m @ 0.2 m |

Figure 9

AIRBORNE TUNABLE MID-IR LASER GAS-CORRELATION SENSOR

DISCUSSION OF THE BACKGROUND

1. Field of the Invention

The invention relates to a sensor and method for detecting natural gas in the atmosphere.

2. Background of the Invention

Gas correlation is known to be one of the more sensitive optical measurement techniques which uses infrared emission from or absorption of a gas of interest to estimate the concentration of that gas in the sensing environment. The principle of measurement is based on a spectral correlation between a target gas of interest and a correlation gas normally the same as the target gas and contained in a cell inside the sensor. In a typical application, the correlation cell is filled with the target gas of interest to a specific pressure (i.e., concentration) to provide an optical depth at the center of the absorption lines of specific region of the molecular spectral band. The gas cell design (i.e., gas pressure and path length) is designed to obtain maximum sensitivity for the sensor near the target gas burden (i.e., the concentration times the pass length).

In general, the optimum gas cell provides a sufficiently large optical depth at the line centers of the absorption band of the gas of interest but not so large that the individual lines are well separated from each other after line broadening. When the spectral band includes a large number of absorption lines of varying strength, optimization becomes quite involved requiring numerical simulation or extensive experiments. To complicate the problem further, optimization typically involves the design of a filter bandwidth for the spectrum of interest. In general, a wide bandwidth is desired to increase the signal throughput and thus the sensitivity. While a conventional laser system may have enough brightness to be used, if it can be tuned to the desired infrared range, a conventional laser system is not suitable due to the narrow spectral line features of the laser radiation.

Passive gas correlation techniques as described by Lee and Zwick, 1985 and Ward and Zwick, 1975 (referenced below) use natural infrared radiation sources from either the ground or the sky radiance depending on the environment. The performance of passive gas correlation techniques depend on the temperature difference between the atmospheric gases and the Earth's surface. Also changes in the surface reflectivity and inhomogeneity in the background can give rise to serious errors with the passive technique and make it difficult to quantify the gas concentration in real time.

Active gas correlation techniques have been implemented in the laboratory (i.e., a stationary setup) whereby a high temperature source can be directly located in the sensor field of view. A high temperature blackbody source can be used as an active illumination source, but utilization of a blackbody source is not practical in many applications. Conventional high temperature blackbody sources have a limited emitting surface area and are substantially smaller than the field of view (FOV) or foot print of the sensor. Even though the temperature of the active source can be a magnitude or more higher than the room temperature source, the effective radiance of such a source at the infrared region does not increase significantly due to the specific nature of blackbody radiation. Thus, normally a large area low temperature blackbody source is used for active gas correlation measurement in the laboratory setting.

Active gas correlation techniques also differs from differential absorption lidar (DIAL) commonly used for remote gas measurement (Warren, 1996, Quagliano, et al, 1997, Prasad and Geiger, 1996). DIAL measurement uses two different wavelengths, one on the absorption line and one off the absorption line, provided by either two lasers or one laser whose wavelength can be switched (Lee et al, 2004, Prasad et al, 1998). Active gas correlation techniques utilize a single output pulse centered on the absorption line of the target gas. However, the spectral bandwidth of the laser should be broad enough to at least partially overlap the chosen absorption line (or lines) of the target gas, unlike the DIAL technique wherein the laser spectral bandwidth is commonly chosen to be much narrower than the width of the absorption line. One advantage of an active gas correlation technique over DIAL is that the active gas correlation sensor makes two measurements simultaneously on an identical column-content concentration of target gas, while the DIAL system's sequential measurement intrinsically probes different columns differing by the pulse sequence, different albedos for the two pulses and/or wavelengths, and speed of the platform movement. The following articles describing the development of gas correlation techniques are incorporated herein by reference in their entirety:

1. Lee, H. S. and H. H. Zwick, "Gas Filter Correlation Instrument for the Remote Sensing of Gas Leaks", Review of Scientific Instruments, vol 56, no 9, pp 1812-1819, September 1985;
2. Ward, T. V. and H. H. Zwick, Applied Optics, vol 14, pp 2896-1536, 1975.
3. Ben-David, A., "Optimal bandwidth for topographical differential absorption lidar detection", Applied Optics, vol 35, no 9, pp 1531-1536, 1996;
4. Warren, R. E., "Optimum detection of multiple vapor materials with frequency-agile lidar", Applied Optics, vol 35, no 21, pp 4180-4193, 1996;
5. Prasad, N. S. and A. R. Geiger, "Remote sensing of propane and methane by means of a differential absorption lidar by topographic reflection", Optical Engineering, vol 35, pp 1105-11, 1996;
6. Prasad, C. R., P. Kabro and S. L. Mathur, "Tunable IR differential absorption lidar for remote sensing of chemicals", Application of Lidar to Current Atmospheric Topics III, SPIE, vol 3757, 87-95, 1998;
7. Quagliano, J. R., P. O. Stoutland, R. R. Petrin, R. K. Sander, R. J. Romero, M. C. Whitehead, C. R. Quick, J. J. Tiee and L. J. Jolin, "Quantitative chemical identification of four gasses in remote infrared (9-11 ?m) differential absorption lidar experiments", Applied Optics, vol 36, no 9, pp 1915-1927, 1997;
8. Lee, H. S., C. R. Prasad and J. Zhang "Tunable IR laser for MALDI", U.S. Pat. No. 6,683,984, (2004); and
9. Sandsten, J., H. Edner and S. Svanberg, "Gas imaging by infrared gas-correlation spectrometry", Optics Letters, 21, 23, 1945-1947, 1996.

SUMMARY OF THE INVENTION

In one embodiment of the present invention, there is provided a method for measuring target gas concentrations in an atmosphere. The method emits in the atmosphere a laser beam tuned to a molecular absorption line of a target gas, the laser beam having a spectral bandwidth greater than a full width of the molecular absorption line of the target gas. The method receives a reflected signal affected by gas absorption of the target gas, divides and directs the received signal into a first optical path and a second optical path (including in one of the paths a correlation gas cell filled with a predetermined concentration of the target gas), detects transmitted signals through the first optical path and the second optical path, and calculates a target gas concentration by comparing a first signal transmitted through the first optical path to a second signal transmitted through the second optical path.

In one embodiment of the present invention, there is provided an apparatus for measuring target gas concentrations in an atmosphere that includes a laser source tunable to a specific molecular absorption line of a target gas and configured to emit in the atmosphere a laser beam having a spectral bandwidth greater than a full width of the molecular absorption line of the target gas. The apparatus includes a receiver configured to receive a reflected signal affected by gas absorption of the target gas in an optical path of the laser beam, and includes at least one detector configured to detect transmitted signals through the first optical path and the second optical path.

It is to be understood that both the foregoing general description of the invention and the following detailed description are exemplary, but are not restrictive of the invention.

BRIEF DESCRIPTION OF THE DRAWINGS

A more complete appreciation of the present invention and many attendant advantages thereof will be readily obtained as the same becomes better understood by reference to the following detailed description when considered in connection with the accompanying drawings, wherein:

FIG. 7 is a table depicting specifications for a tunable mid-IR laser/OPO source for gas sensor, according to one embodiment of the present invention;

FIG. 8 is a table depicting parameters used in the simulation of performance of the active gas correlation sensor, according to one embodiment of the present invention;

FIG. 9 is a table depicting baseline specifications for a airborne tunable mid-IR laser gas correlation sensor, according to one embodiment of the present invention;

DETAILED DESCRIPTION OF THE EMBODIMENTS

Figure 1:
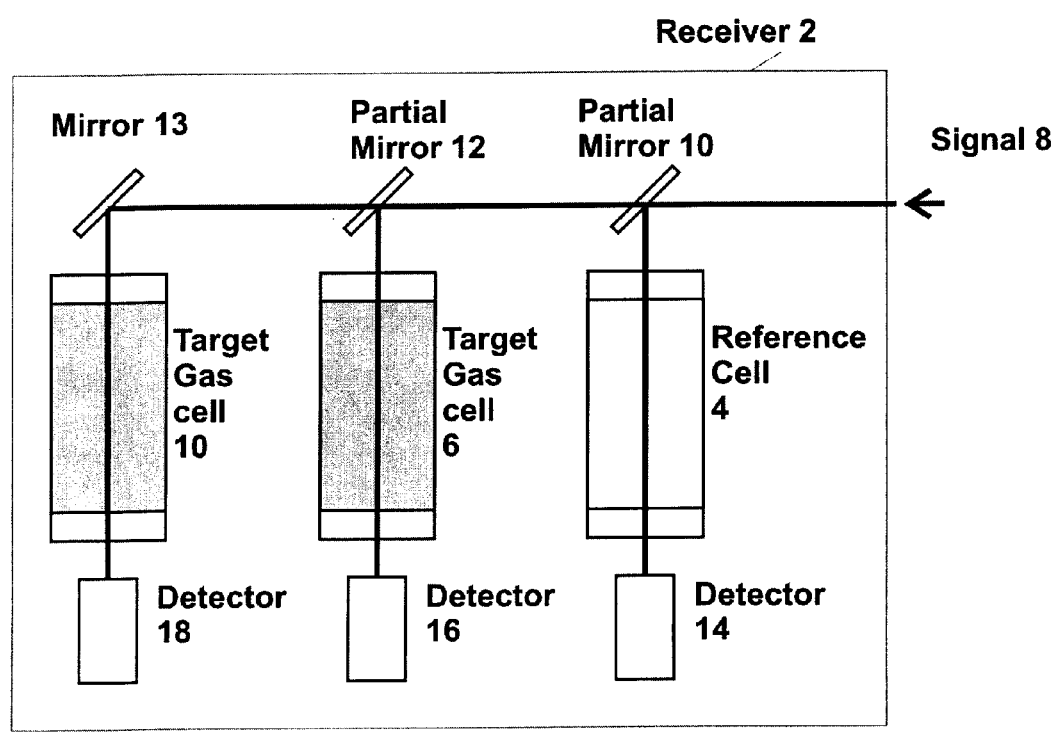
FIG. 1 is a schematic illustration of a laser gas correlation sensor receiver according to one embodiment of the present invention.

Referring now to the drawings, wherein like reference numerals designate identical, or corresponding parts throughout the several views, FIG. 1 is a schematic representation of a laser gas correlation sensor receiver 2 according to a non-limiting embodiment of the present invention. As shown in FIG. 1, incoming radiation signal 8 which is affected by the target gas outside the sensor system, is divided into two or more paths. One path is directed to a correlation gas channel (or the "on" line channel), and another path is directed to a reference gas channel (or the "off" line channel). As shown illustratively in FIG. 1, the sensor receiver 2 includes a reference cell 4 (i.e., the "off" line channel) filled with a non-target gas having spectrally inert characteristics such as for example air. The sensor receiver 2 includes a target gas cell 6 (i.e., the "on" line channel) filled with a target gas providing a known absorbance over a known optical distance (i.e., the interior distance across the target gas cell 6). As shown illustratively in FIG. 1, when a signal 8 from a telescope is received by the sensor receiver 2, partial mirrors 10 and 12 divide and transmit the received signal through the reference cell 4 and the target gas cell 6, respectively, and mirror 13 transmits the remaining signal through a second target cell 10, forming three optical channels. The gas cells 4, 6, and 10 in one embodiment of the present invention can be made of stainless steel (or anodized aluminum), with two $CaF_2$ seal windows that contain a one-atmosphere (or other higher or lower) concentration of the gas to be detected. For example, either a one-atmosphere of methane or a mixture of air and methane can be sealed within one target cell (e.g., target cell 6) and either a one-atmosphere of ethane or a mixture of air and ethane can be sealed within the second target cell (e.g., target cell 10). Air at one atmosphere can be an example of the reference cell 4. The diameters of the gas cells 4, 6, and 10 can be for example 25 mm and variable in length. Detectors 14, 16 and 18 respectively detect signals transmitted through the reference cell 4 and the target gas cell 6, respectively. Thermoelectrically-cooled InAs detectors are used as the detectors 14, 16 and 18 in one embodiment of the present invention.

When there is no target gas present in the path of the beam outside the sensor receiver 2, the incoming radiation will only be strongly absorbed by the respective ones of cells 6 and 10 (i.e., the correlation cells), but not by the reference cell 4. Thus, the net signal difference (i.e., "on" channel of one of the correlation cells minus "off" channel of the reference cell) will be negative. On the other hand, when the incoming radiation has been absorbed by target gas in the atmosphere (i.e., outside the sensor), the signal from the "on" channel is not substantially different from the previous case (where there was no target gas) because the additional optical thickness of the target gas when combined with the already large optical depth of the correlation cell makes no substantial change (i.e., it is still optically thick). Thus, no net change occurs. In contrast however, the off channel signal will be reduced by the amount of the absorption by the target gas. As a result, the net difference signal (on minus off signal) will be less negative than for the no target gas case.

In one embodiment of the present invention, inter-channel sensitivity calibration balances the off/on channel signal in the absence of the target gas in the incoming radiation. This calibration balances the optical efficiency difference between the on and off channels due to the correlation gas absorption as well as difference in transmittance of other optical components in the beam path. To ensure that the two channels provide nearly equal response to equal signal inputs, the calibration determines if it is necessary to compensate either one or the other channel. This occurs if the optical efficiency of either of the two channels is significantly different from the other. Gas sensitivity can be further calibrated in the laboratory using known quantities of the target gas at varying concentrations.

In operation, the incoming laser optical signal from the receiver telescope is split and one portion is sent through the cell to one detector and the second and third portion are sent directly to the second and third detector (see FIG. 1). These detectors can be for example InAs detectors. Detected laser signals on the two pairs of channels (i.e., detectors 14 and 16, detectors 14 and 18) are then available for correlation as a mechanism of measuring trace gases (e.g., methane, and ethane) concentration in an atmospheric column for example beneath an aircraft. Detector electrical outputs can be coupled into a trans-impedance amplifier and analog-to-digital converter for digitization and storage of the lidar signal pulse that is backscattered from the Earth surface. In this embodiment, a laser pulse repetition rate of 100 Hz (or higher) can be used. In the data analysis system of one embodiment of the present invention, the photo-detector converts the optical return signal into a photo-voltage, then the amplifier amplifies the signal.

In infrared detection, the low frequency (l/f) noise and baseline drift are important factors. Baseline drift can be corrected for example by measuring the detector signal before and after every pulse to correct for any drift and noise. The laser pulse returns can be measured in the three channels nearly if not in fact simultaneously, and are recorded for example as signal (A) signal (B) and signal (C). Signal (A) represents the direct laser atmospheric column return signal through the air filled reference cell, and signal (B) represents the return signal that passes through the methane filled gas correlation cell and signal (C) represents the return signal that passes through the ethane filled gas correlation cell.

Figure 2:
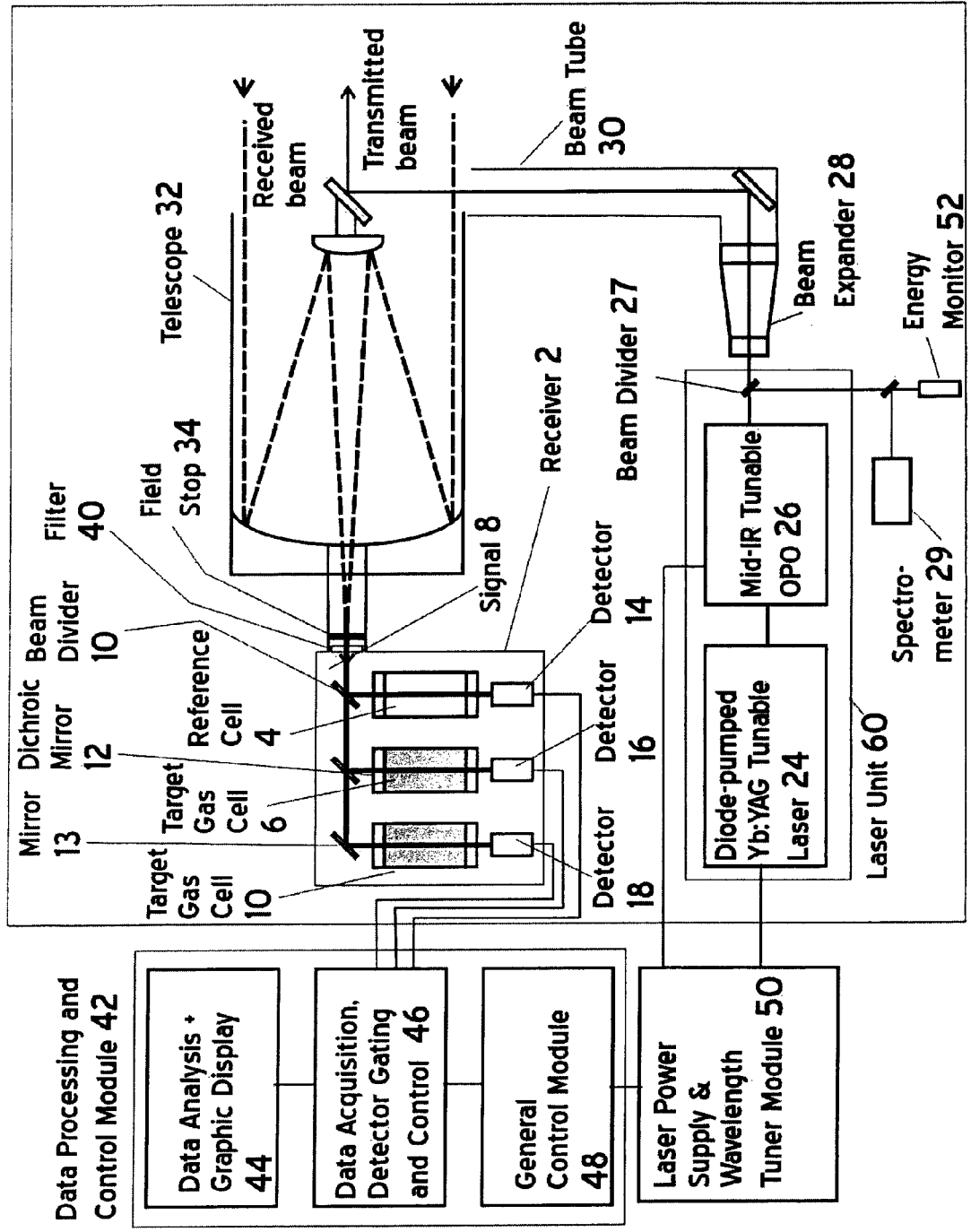
FIG. 2 is a schematic illustration of an airborne tunable mid-IR laser gas correlation sensor according to one embodiment of the present invention.

FIG. 2 is a schematic illustrating one configuration for sensor system 20 of the present invention. One feature includes a laser 24 which in one non-limiting embodiment is a tunable diode laser and in another (non-limiting) embodiment transmits laser radiation in the mid-IR wavelength range (e.g., 2.8 to 4.2 µm). A non-limiting example of a suitable laser for the present invention is shown in FIG. 2, and includes: 1) a tunable diode-pumped Yb:YAG laser 24 that is configured to produce 100 Hz pulse repetition rate, 7~8 mJ pulse energy at 1.03 µm and $TEM_{00}$ mode output, and 2) quasi-phase-matched periodically poled lithium niobate (PPLN) Optical Parametric Oscillator (OPO) 26 pumped by the above-noted Yb:YAG laser 24. The OPO 26 can be configured to produce ~1 mJ of output energy for a tuning range of 2.8 to 4.2 µm. The output spectral band width is considered broad (e.g., 3 to 6 nm). Detailed specifications of the mid-IR laser that forms one example of the Yb:YAG laser 24 and the OPO 26 are listed in Table 1 of FIG. 7. Table 1 shows one example where the spectral width of output line width is 3 to 6 nm. The line width is wider that that of conventional lasers which usually have an output line width of <0.5 nm. For gases such as methane, ethane, carbon dioxide, etc, linewidths of the order of 3 to 6 nm are adequate to achieve high performance. But for other gases with more complex or very dense spectra linewidths as wide as 10 nm may be needed. It is possible to generate linewidths of 10 nm with the laser system described here. Thus, the spectral bandwidths of the lasers in various embodiments of the present invention are greater than a molecular full width of a target gas of interest, or greater by a factor of 30-100 times (or in some embodiments greater than 50).

FIG. 2 shows a tunable laser 24 pumping a tunable mid-IR OPO (Optical Parametric Oscillator) 26 which in turn outputs laser radiation to a beam expander 28. A beam tube 30 blocks scattered light while the laser radiation is transmitted from the sensor system 20. A receiver telescope 32 collects light reflected back to the sensor system 20 and focuses the returned light to the sensor receiver 2. In one embodiment of the present invention, the receiver telescope 32 is a 200 mm diameter f/10 telescope with a tube length of only 125 mm is used as the receiver, providing for efficient collection of mid-IR laser backscatter signals. The primary and secondary mirrors can be gold-coated to produce a reflection of 98% over the 3 to 4 µm infrared wavelength region for very-efficient lidar detection. This telescope design can produce a high image quality to permit coupling of all the received laser radiation on to small diameter detectors. The complete receiver package in one embodiment of the present invention can attach directly to the back of telescope. The receiver package 2 includes an optical bench provided with two or more channels. The receiver package 2 permits a configuration for convenient mounting and alignment of the gas cells 4, 6, and 10, detectors 14, 16, and 18, filters 40 and other optical components, and detector components. The detectors 14, 16, and 18 can be InAs detectors cooled with thermoelectric coolers to reduce detector noise to an acceptable level that to achieve a high signal to noise ratio with the lidar backscatter signal.

A number of processing and control modules 42 are shown in FIG. 2 and can be included to control operation of the lasers and detectors and to process the received signal information in the manner described below. These processing and control modules include a data analysis and graphics display module 44, a data acquisition, detector gating and control module 46, a general control module 48, and a pump laser power supply and wavelength tuner module 50.

In one embodiment of the sensor system 20 of the present invention (with the laser operating at a repetition rate of for example 100 Hz), measurements can be completed rapidly which allows an increased area coverage from moving platforms and achieves a spatial resolution of the order of meters. Further improvements in sensitivity can be achieved in one embodiment of the present invention by signal averaging. In one embodiment of the sensor system 20 of the present invention, an energy monitor 52 can be utilized to determine laser energy values on a shot by shot basis and can be used to normalize the signals for laser energy fluctuations.

The sensor system 20 can be a mobile sensor. The sensor system 20 can perform aerial surveys over large regions for natural gas (e.g., natural gas, petroleum products, methane, ethane) and other related hydrocarbons when operated from mobile platforms, such as trucks or low-altitude aircraft. The sensor system 20 can achieve both high sensitivity and high measurement throughput rate by combining a gas correlation technique with a wide bandwidth tunable mid-IR laser.

The sensor system 20 can include a lidar sensor that measures the total column-content concentration of methane in the atmospheric path below the aircraft by reflecting the laser pulses off the ground, water or any other surface. Combining the wide band laser source with the gas correlation lidar technique provides several advantages: 1) effects of variations in the albedo of the surface are eliminated by gas correlation method where the two channel measurements that are made using the identical foot print, 2) increased accuracy and sensitivity resulting from the use of active laser source for signal measurement instead of relying on the temperature contrast between the target gas and the radiation source that is used in passive gas correlation technique, and 3) larger spatial coverage, better spatial resolution resulting from the use of a solid state laser with a high pulse repetition frequency (100 Hz).

Figure 3:
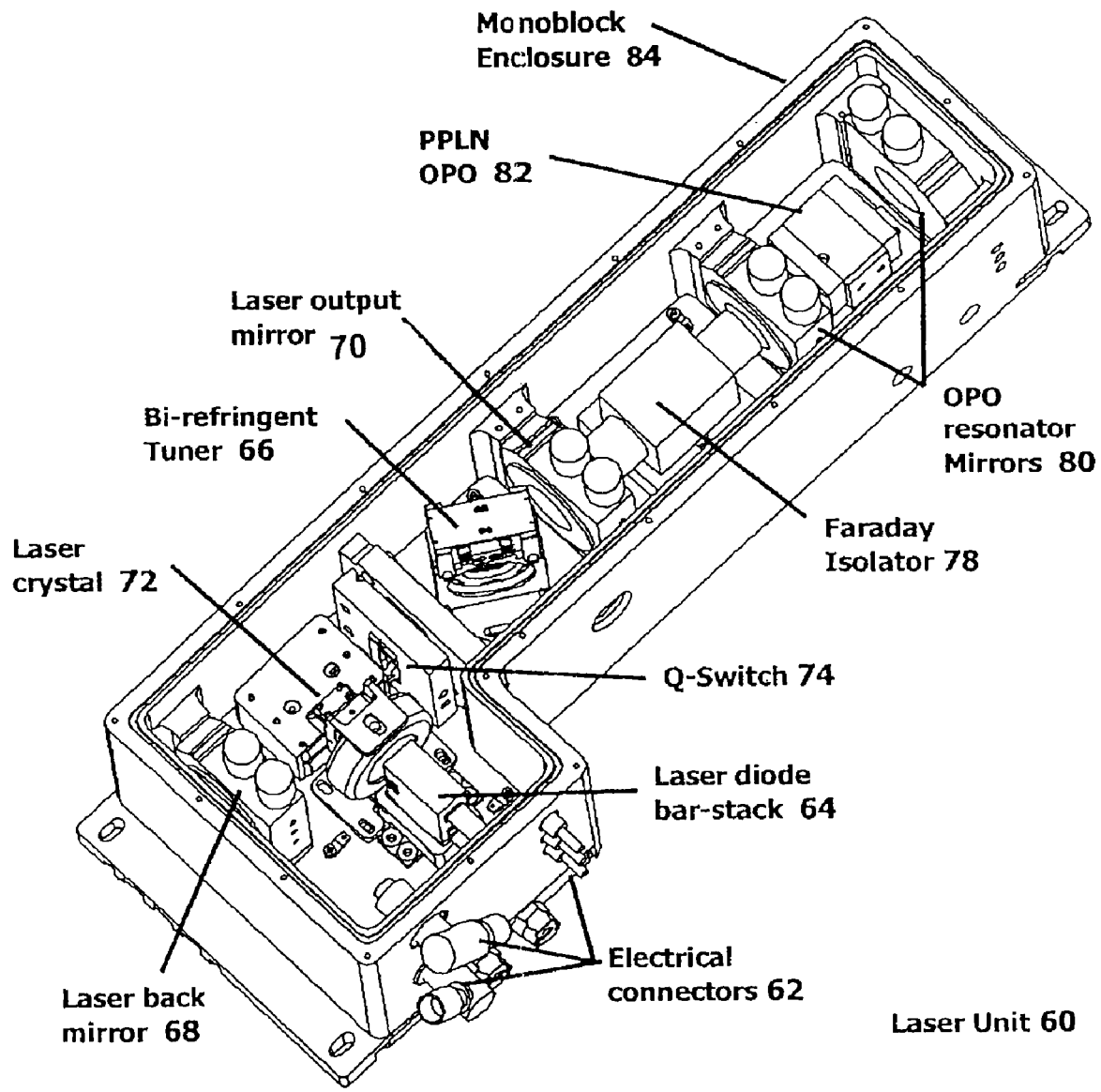
FIG. 3 is a schematic illustration of a mid-IR laser enclosure design and construction according to one embodiment of the present invention.

FIG. 3 shows a configuration according to one embodiment of the present invention of a mid-IR laser unit 60. In one embodiment of the present invention, the overall dimensions can be 14" (L)×4" (W)×4.5" (H) making the mid-IR laser unit 60 a compact system. Electrical connectors 62 attach to one wall of the unit 60, as shown in FIG. 3, and provide power to the laser diode bar stack 64, the Q-switch 74 and PPLN oven 82. The mid-IR laser system 60 includes a laser back mirror 68 and a laser output mirror 70 forming a laser cavity. Within the laser cavity are a laser crystal 72, the Q switch 74, and the bi-refringent tuner 66. The mid-IR laser system 60, as shown in FIG. 3, includes a Faraday rotator optical isolator 78, OPO resonator mirrors 80 and PPLN OPO in a temperature controlled oven 82. The mid-IR laser unit 60, as shown in FIG. 3, is contained in a monoblock enclosure 84 serving to provide stability to the optical components, especially when these components are part of a mobile gas sensor.

Gas-Correlation Sensor Analysis

The gas correlation technique of the present invention can eliminate or reduce interference effects due to laser signal absorption from species other than the measurement objective (e.g. methane gas). However, the laser signal absorption from other species can reduce the received signal and thus reduce the measurement sensitivity of the sensor. In order to obtain both high sensitivity and high measurement throughput rate, as detailed below, the selection of an optimal methane spectral region is utilized in one embodiment of the present invention.

Figure 4:
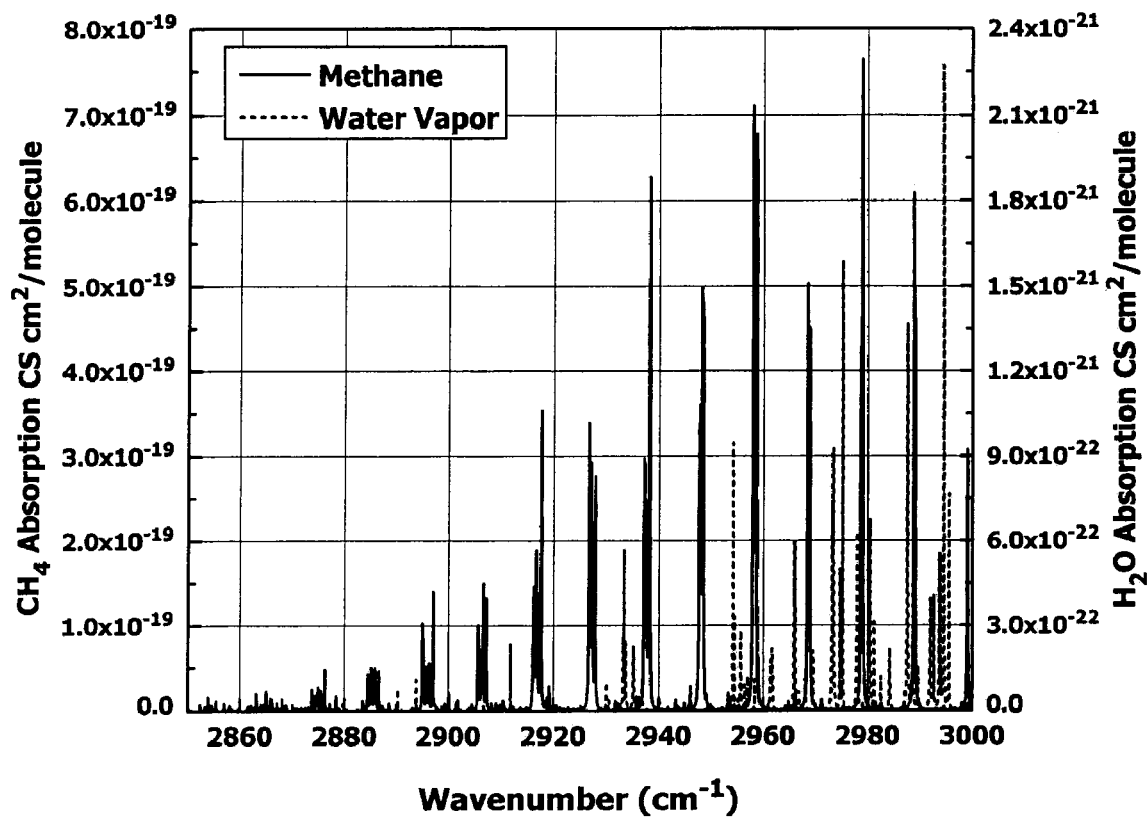
FIG. 4 is a schematic illustration of a high resolution absorption spectrum of methane and water vapor calculated from HITRAN, according to one embodiment of the present invention.
Figure 5:
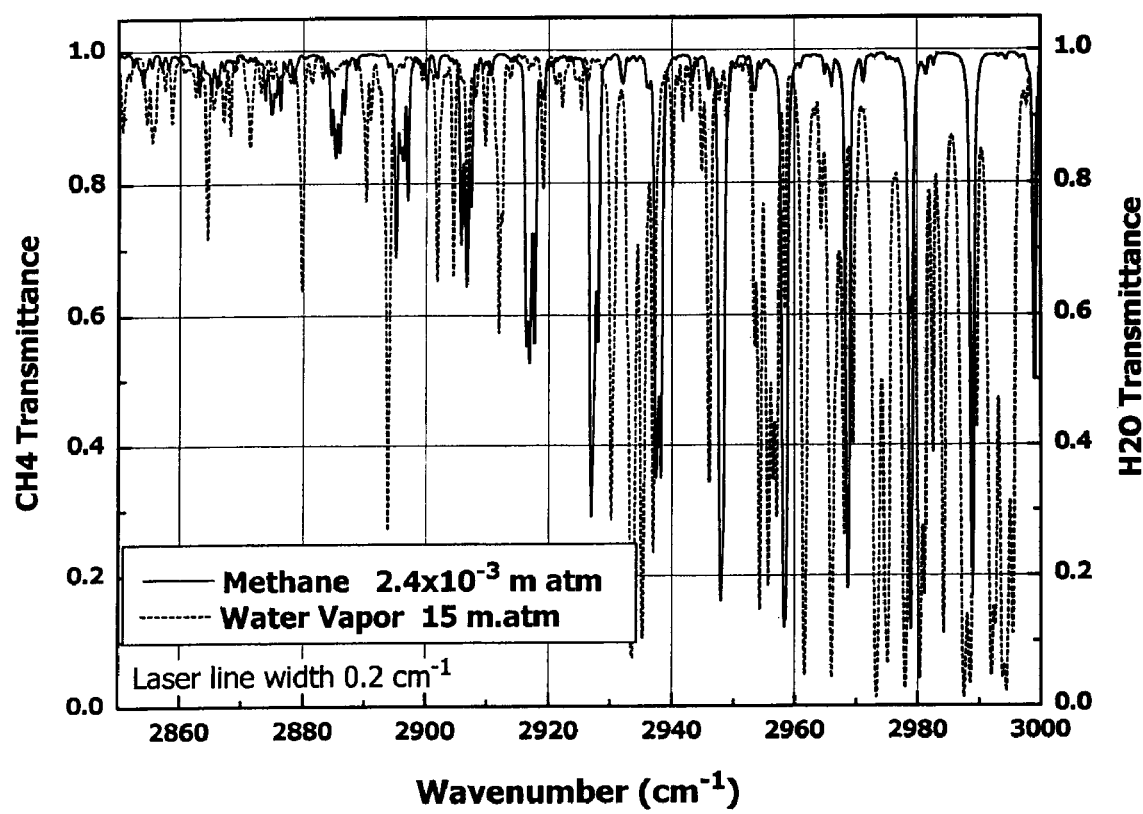
FIG. 5 is a schematic illustration of atmospheric transmittance in the mid-IR, including absorption by methane and water vapor, according to one embodiment of the present invention.

Of the various atmospheric gases, water vapor is one interference gas in the mid-IR region. FIG. 4 shows the atmospheric transmittance for methane and water vapor absorption. The wavelength region from 2915 cm$^{-1}$ to 2919 cm$^{-1}$, centered at 2917 cm$^{-1}$ was found to be less contaminated by water vapor interference, and is thus one suitable wavelength for the sensor of the present invention. FIG. 5 shows a synthesized high-resolution atmospheric spectrum transmittance calculated for the region from 2915 cm$^{-1}$ to 2919 cm$^{-1}$ using data from the HIgh-resolution TRANsmission molecular (HITRAN) atmospheric spectroscopy database created by US Air Force Geophysics Laboratory, Hanscom AFB, MA). From FIG. 5, it is evident that a laser line width in the range of 3 to 6 cm$^{-1}$ is adequate to cover the isolated group of methane absorption lines at 2917 cm$^{-1}$ for high-sensitivity lidar gas correlation measurements.

Figure 6:
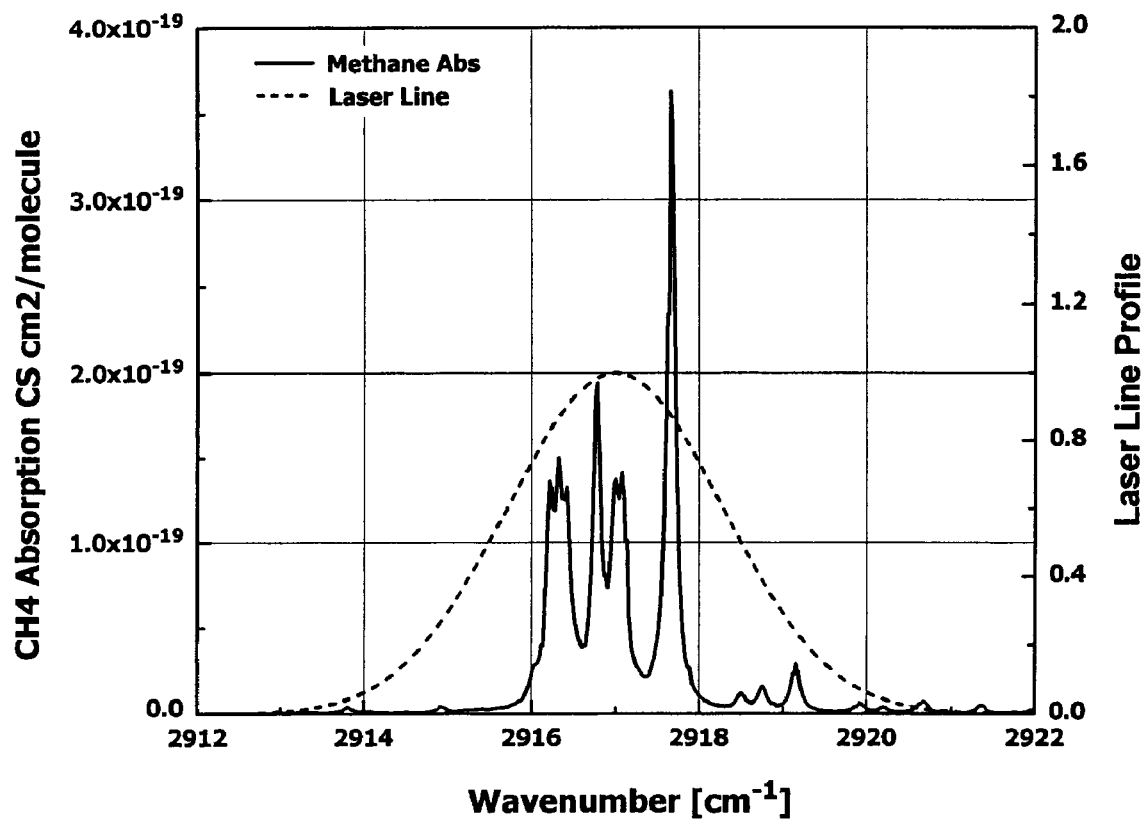
FIG. 6 is a graph showing simulated atmospheric methane absorption and laser profile over a range from 2912 $cm^{-1}$ to 2922 $cm^{-1}$.

Measurement of atmospheric methane by the gas correlation lidar, as in one embodiment of the present invention, has been simulated by assuming an atmospheric methane concentration of 1.7 ppm and a measurement distance (i.e., the aircraft altitude or atmospheric column) of 1 km. FIG. 6 is a graph showing simulated atmospheric methane absorption and laser profile over a range from 2912 cm$^{-1}$ to 2922 cm$^{-1}$. Assuming the laser line center to be located at 2917 cm$^{-1}$, and a line width of 3 cm$^{-1}$, the two-way atmospheric transmittance is calculated to be about 64% by the simulation, while the transmittance becomes about 76% for a 5 cm$^{-1}$ laser line width.

In one embodiment of the present invention, the sensor can maximize the signal-to-noise ratio (SNR) for a given set of wavelengths and measurement geometry. The SNR can be increased by optimizing the transmitted and received laser signals and by reducing the limiting noise figure of the system. Modeling of airborne gas correlation lidar utilized a laser pulse of duration $\tau_p$ and energy $E_L$ transmitted into the atmosphere and showed that laser radiation is absorbed by methane along a lidar signal propagation over the two-way path from the lidar sensor to and from the Earth surface reflection. A portion of the backscattered laser signal pulse is collected with a telescope of area A. The received signal is then given by the standard lidar equation below.

$$E_s(\lambda_L, R) = E_L(\lambda_L) \cdot \eta \cdot \phi(R) \cdot \rho(\lambda_L) \cdot \frac{A}{\pi \cdot R^2} \cdot \exp\left(-2 \cdot \int_0^R K(\lambda, z) \cdot dz\right)$$

The lidar collected signal energy $E_S$ from the telescope is a function of the transmitted laser energy $E_L$, receiver optical system efficiency $\eta$, geometric overlap function $\Phi(R)$ between transmitter and receiver optical patterns, range R from telescope to Earth surface, laser surface reflectivity $\rho$, and the absorption K due to the species of interest. The parameters listed in Table 2 of FIG. 8 were used in the model calculation of the laser gas correlation sensor of the present invention. With a 64% transmittance and a 25 ns laser pulse, the optical signal received at the InAs detector is 3.2 µW.

Using a typical thermo-electrically-cooled InAs detector (e.g., from Judson technologies), the signal to noise ratio (SNR) of the active gas correlation sensor system of $$NEP = \frac{\sqrt{A_d \cdot BW}}{D^*}$$

the present invention was calculated. The total noise contributions to the detection process were estimated. A straight-forward method is to estimate the noise equivalent power (NEP) in watts (W) from the value of detectivity D*[cm Hz$^{1/2}$/W] of the detector furnished by the manufacturer. The following expression for NEP is given in terms of detector size and detectivity D*. For the chosen detector, the size is 1 mm in diameter, D* is 4.1×10$^{10}$ cmHz$^{1/2}$/W, and BW is 20 MHz. The result is a NEP of 9.7×10$^{-9}$ W or 9.7 nW. This result predicts a detected signal with a SNR=330 (i.e., SNR=25 db).

Based on this SNR, the limiting detectable burden concentration for the simulation of sensing methane for a 1 km column of atmosphere is 10 ppm·m with SNR of one. Since the gas-correlation technique of the present invention can use two detectors, this increases the detection limit to 14 ppm·m due to the addition of the two independent noise sources from each detector. Further, since this simulation applies to a single laser pulse, this implies that the detection limit for the present invention can be achieved in an observation time of only 0.01 sec, permitting rapid assessment of methane gas concentration.

Table 3 of FIG. 9 summarizes the laser gas correlation sensor parameters that can be used to conduct a methane measurement in the present invention. The measurement concept is based on column-content measurement from a low-altitude aircraft. In one embodiment of the present invention, the laser measurement of methane can be conducted continuously as the aircraft flies in a terrain-following trajectory for example at ~1 km altitude. This is nominally within a "well-mixed" atmospheric boundary layer. The measured methane concentration would be indicative of an average to the total atmospheric column beneath the aircraft.

The simulation shows that the present invention can achieve <14 ppm·m in 0.01 sec (i.e., for each laser pulse at 100 pps rate). This corresponds to ~1.5 m horizontal resolution along the aircraft trajectory for an aircraft flying at ~100 knots ground speed. If this horizontal resolution is in excess of measurement requirements, additional measurements at the 100 pps rate can be used by averaging to improve the measurement sensitivity along the flight track (at the expense of horizontal resolution) or used in a cross-tracking scanning scheme to produce a swath-width of methane concentration measurements.

For example, a lidar unit mounted in/on a van can be used to measure pollution over a highway. In this example, a beam can be transmitted over a range that can vary from a few hundred meters up to 2 km and hit a reflector (such as a highway sign, the side of a building, tree or some other feature) or hit the ground and be reflected.

Figure 10:
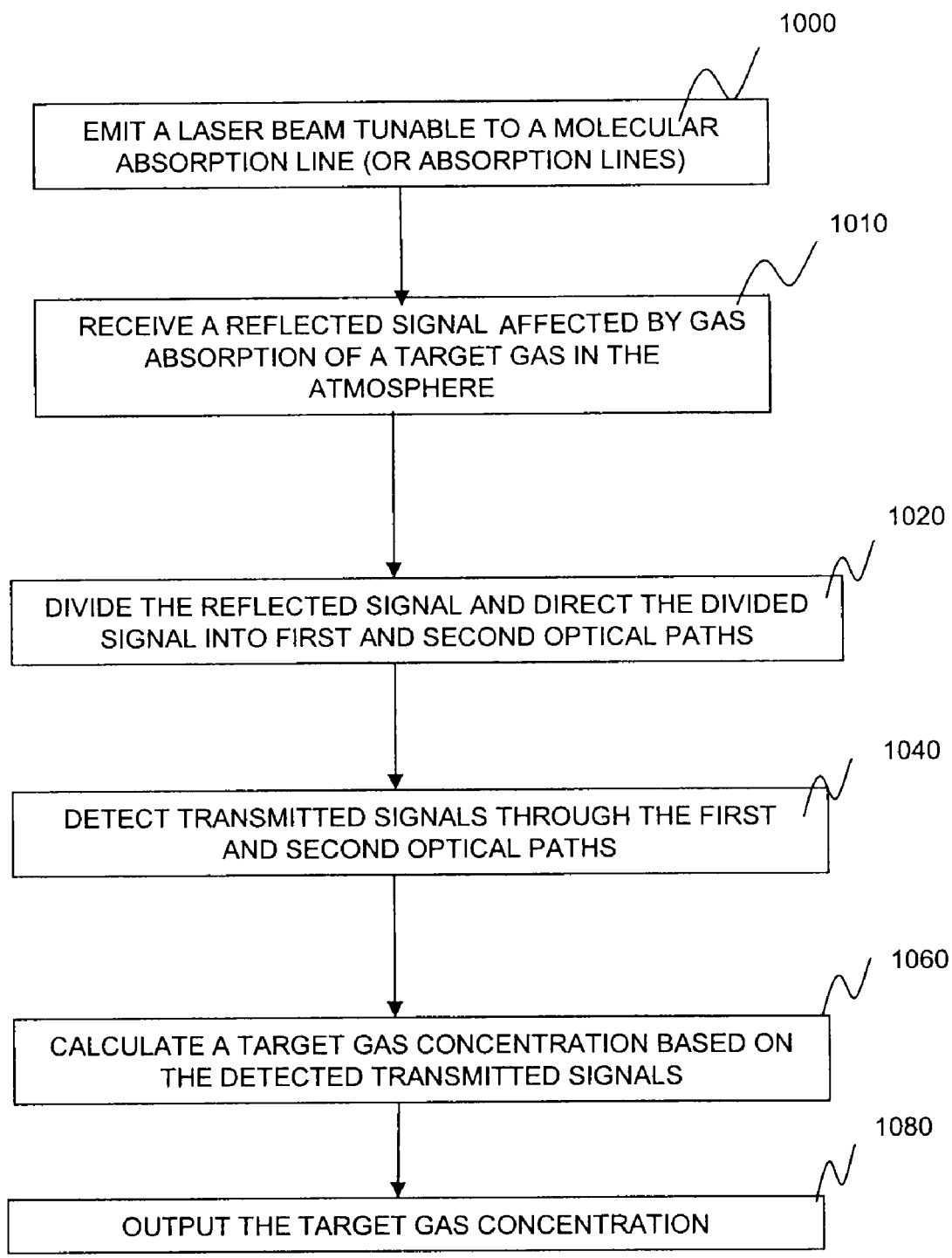
FIG. 10 is a flowchart depicting a generalized flowchart according to one method of the present invention.

FIG. 10 is a flowchart depicting a generalized flowchart according to one method of the present invention for measuring target gases in the atmosphere. At step 1000, a laser beam tunable to a molecular absorption line of a target gas is emitted. At step 1010, a reflected signal affected by gas absorption of the target gas in an optical path of the laser beam is received. At step 1020, the received signal is divided and directed into a first optical path and a second optical path. One of the optical paths includes a correlation gas cell filled with a predetermined concentration of the target gas. At step 1040, transmitted signals through the first optical path and the second optical path are detected. At step 1060, a target gas concentration is calculated by comparing a first signal transmitted through the first optical path to a second signal transmitted through the second optical path. At step 1080, the calculated target gas concentration is provided as an output. The output can be displayed to a user or provided to a processor mapping the target gas concentration in the atmosphere. The output can be provided by remote communication to those in vicinity of the target gas. The output can be provided to a system that is tracking a cloud of the target gas as its concentration and extent changes with time.

Figure 11:
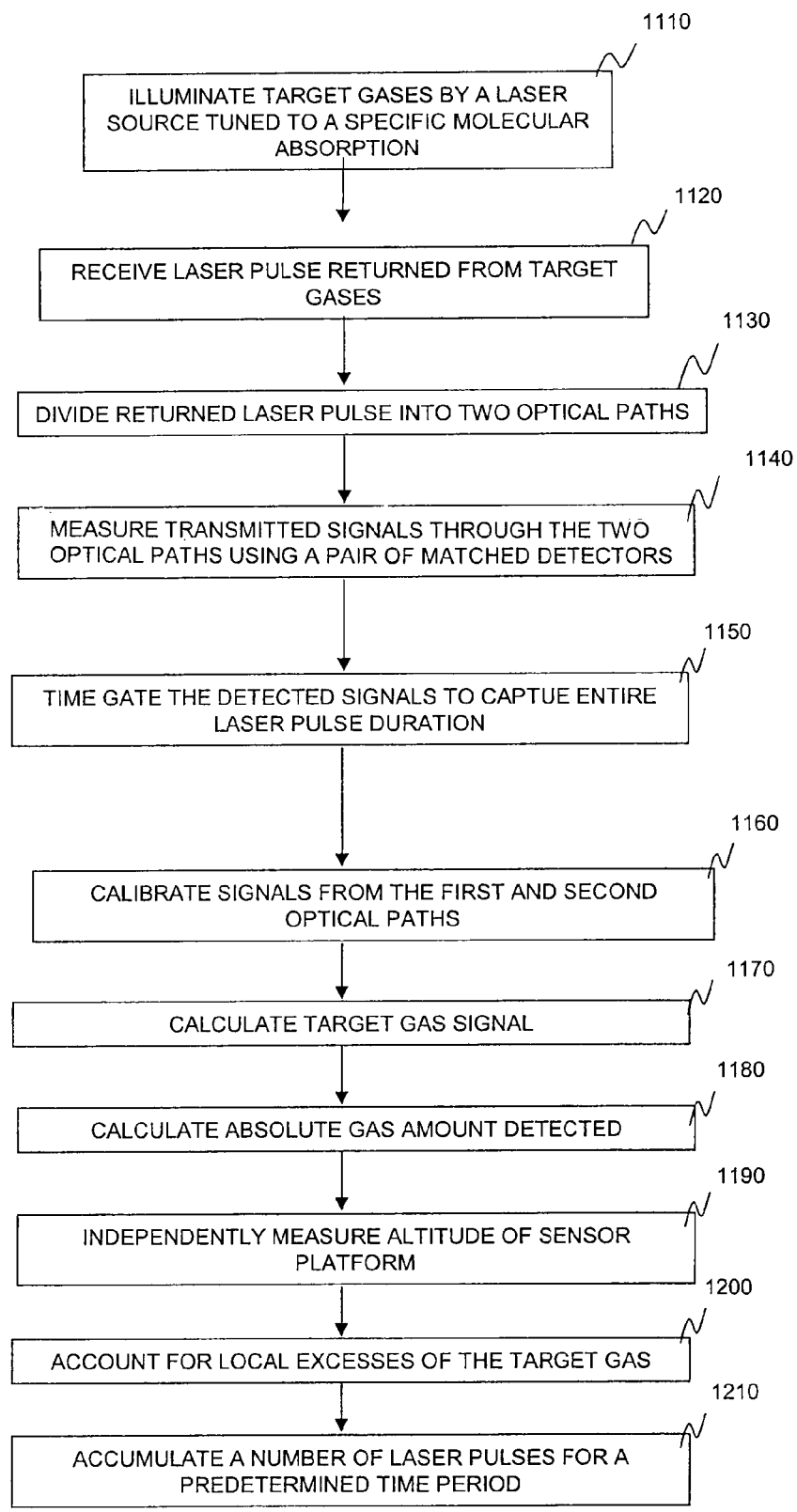
FIG. 11 is a flowchart depicting a detailed method according to the present invention.

FIG. 11 is a flowchart depicting a detailed method according to the present invention for measuring atmospheric gases by active gas correlation. At step 1110, the target gases are illuminated by a laser source tuned to a specific molecular absorption line. At step 1120, the laser pulse affected by the gas absorption is returned to the receiver of the sensor via diffuse reflection from the ground (in case of airborne application), or other hard targets. At step 1130, the collected return laser pulse is divided and directed into two optical paths: one path (i.e., the first optical path) with a neutral (reference) gas cell and another path (i.e., the second optical path) with a correlation gas cell filled with the target gas of optimal concentration and thickness, in front of a pair of detectors.

At step 1140, a pair of matched (i.e., nearly identical as from the same vendor) detectors measure the transmitted signals independently and simultaneously. For example, the two cooled-photo-detectors in FIG. 1 have the same performance and specifications.

At step 1150, the detector signal is time gated to capture an entire laser pulse duration just in time upon its arrival to the detector and integrated for the duration and digitized with a high precision required for sensor sensitivity requirement. This rejects the scattered laser light from within the sensor and near field and minimizes the background effect by rejecting the cw components at all times except during the allowed gating period of only a few hundred nanoseconds as against the milliseconds of time between the pulses.

Steps 1160-1210 are optional steps used in the present invention. At step 1160, signals from off/on channels (i.e., from the first and second optical path) are calibrated for the final digitized signals from each channel by determining the optical efficiencies of the two channels. If the optical efficiencies of the two channels are unequal, the signals in each channel are corrected by multiplying by the inverse of the optical efficiency of the channel so that the channel outputs are balanced. At step 1170, the target gas signal is calculated by subtracting the reference cell signal from the correlation gas cell signal and dividing its value by the correlation cell signal for normalization. At step 1180, the signal for the absolute gas amount of the gas burden is calculated based on Beer's law and absorption strength of the specific absorption line. Gas burden defined as the product of gas concentration and the path length.

At step 1190, the altitude of the sensor platform (the path length of the laser beam) is independently measured by the arrival time of the laser return pulse. At step 1200, the atmospheric background gas concentration is computed using the measured path length of the beam and the gas burden calculated from the data over the survey area. An average background gas concentration is then determined by averaging the measurements over the entire area.

At step 1210, local excesses of the target gas are determined by subtracting the background signal from the total signal. If the target is a specific gas—e.g., methane, the atmosphere naturally contains a small amount of methane—about 1 to 2 ppm (referred here as the natural background concentration). But in areas where natural gas deposits or petroleum reserves exist, the local concentrations exceed the natural background by substantial amounts. At step 1220, a predetermined number of individual such measurements are accumulated for a fixed time period for the statistical average optimal for the application. For example, averaging for 0.1 sec, and a 100 Hz laser (i.e., 10 laser pulses) will provide a factor of 3 improvement in signal to noise ratio. Increasing the signal to noise ratio improves the sensor's sensitivity. For a 0.1 sec averaging a factor of 10 signal to noise ratio improvement will result if a 1 kHz laser is used. The averaging period that can be chosen for various embodiments depends on the application and the aircraft speed. For example on an aircraft flying at 100 m/sec, it means that a 10 m spatial region is covered during the 0.1 sec averaging. Thus depending on what is the spatial resolution required the averaging time and laser pulse repetition rate are chosen.

The above methods can minimize the effect of background radiation from for example the solar radiation, ambient radiation, and other thermal radiation originating from the ground, correlation gas cell and all other optical components in the sensor package. The spectral brightness of the illuminating laser pulse used in the present invention is many orders of magnitude greater than that of any of the black body sources conventionally used.

The above methods can be highly selective for a given hydrocarbon gas by choice of the optimal absorption line with proper absorption strength and isolation from other interference gas absorption lines, and are applicable for various gases due to the abundance of the absorption lines in the mid infrared region.

The above methods can provide absolute sensitivity of the gas sensing regardless environmental variation and laser pulse energy variation due to the differential measurement and radiometric calibration.

The above methods can permit a large aerial mapping of the gas concentration with high accuracy and precision based on the absolute sensitivity of the system. The stability of the sensitivity is one requirement for many airborne applications covering a large area such as exploration or environmental studies, as well as a long term trend study at a fixed location. The special features of the gas correlation technique—where the return signal is split into two parts and then ratioed bring remarkable stability to the measurement by removing the effects of laser energy fluctuations, variations in reflectivity of the ground, etc. Thus, it does not depend as heavily on either laser performance stability or structural stability as other techniques such as DIAL do. The sealed Mid-IR laser enclosure design and construction allows the laser to stably operate over long periods of time.

The above methods can reject low frequency components from the received reflected signal. For example, low frequency noise (the 1/f noise) that is present in the detector during the measurement can be removed by measuring the detector signal background just before firing the laser and subtracting it from the signal.

The above methods can provide a common field of view (FOV) for both the first optical path and the second optical path. The techniques discussed above can utilize separate gas cells, with each cell filled with a different target gas and therefore configured to absorb radiation at a specific laser wavelength chosen for that gas. Each cell is thus able to measure the target gas with which it is filled. Accordingly, the optical beams can be passed through different gas cells, and the laser can be tuned to the absorption region specific for each of the gases. For example, the concentration of at least one of methane, ethane, propane, carbon dioxide, carbon monoxide, and oxides of nitrogen can be measured.

The above methods can use a surrogate spectral material in which simulants that can be used instead of the real gas material. For example non-toxic simulants such a $SF_6$ (sulfur hexafluoride), DMMP (dimethyl methylphosphonate), thioglycol (also known as 2-mercaptoethanol: $HSCH_2CH_2OH$), etc are used as surrogates for chemical warfare agents (such as nerve agents, blister agents—mustard, etc).

Numerous modifications and variations on the present invention are possible in light of the above teachings. It is, therefore, to be understood that within the scope of the accompanying claims, the invention may be practiced otherwise than as specifically described herein.

The invention claimed is:

1. A method for measuring target gas concentrations in an atmosphere, comprising:
    emitting in the atmosphere a laser beam tuned to an infrared molecular absorption line of a target gas, the laser beam having a spectral bandwidth greater than a full width of the molecular absorption line of the target gas;
    receiving a reflected signal affected by gas absorption of the target gas;
    dividing and directing the received signal into a first optical path and a second optical path, the first optical path including a correlation gas cell filled with a predetermined concentration of the target gas, the second optical path including a reference cell filled with air or filled with a gas different than the target gas;
    detecting transmitted signals through the first optical path and the second optical path;
    calculating a target gas concentration by comparing a first signal transmitted through the first optical path to a second signal transmitted through the second optical path.

2. The method of claim 1, wherein the emitting a laser beam comprises:
    emitting a laser beam having a spectral bandwidth that exceeds a combined width of a group of molecular absorption lines.

3. The method of claim 1, wherein the calculating comprises:
    subtracting the first signal from the second signal to produce a difference signal; and
    dividing the difference signal by the first signal.

4. The method of claim 1, further comprising:
    emitting as the laser beam a laser pulse having a pulse duration; and
    time gating the received signal to capture an entirety of the laser pulse duration at a detector.

5. The method of claim 1, further comprising:
    calibrating the first and second signals to balance optical efficiency.

6. The method of claim 1, further comprising:
    accumulating a predetermined number of measurements over a time period.

7. The method of claim 1, further comprising:
    rejecting low frequency components from the received reflected signal.

8. The method of claim 1, further comprising:
    providing a common field of view (FOV) for both the first optical path and the second optical path.

9. The method of claim 1, wherein the emitting comprises:
    emitting said laser beam having a spectral bandwidth greater than 100 times the width of the molecular absorption line of the target gas.

10. The method of claim 1, wherein the emitting comprises:
    emitting said laser beam having a spectral bandwidth 30-100 times the width of the molecular absorption line of the target gas.

11. The method of claim 1, wherein the emitting comprises:
    emitting said laser beam having a spectral bandwidth greater than 50 times the width of the molecular absorption line of the target gas.

12. The method of claim 1, wherein the calculating comprises:
    utilizing Beer's law and an absorption strength of the target gas at a wavelength of the laser beam to derive a concentration of the target gas in a path length of the laser beam.

13. The method of claim 1, further comprising:
    measuring multiple gases by using multiple gas cells filled with different target gases.

14. The method of claim 13, further comprising:
    passing optical beams through different gas cells and tuning the laser to the absorption region specific for each of the gases.

15. The method of claim 13, further comprising:
    measuring the concentration of at least one of methane, ethane, propane, carbon dioxide, carbon monoxide, and oxides of nitrogen.

16. The method of claim 13, wherein the calculating a target gas concentration comprises:
    utilizing a simulant of the target gas in one of the multiple gas cells.

17. The method of claim 12, further comprising:
    measuring the path length of the laser beam by the arrival time of the laser beam.

18. The method of claim 17, wherein the calculating comprises:
    determining an atmospheric background gas signal based on the measured path length of the beam and a background signal across an area scanned through repetitive beam emissions.

* * * * *